United States Patent
Kusens

(10) Patent No.: US 9,892,611 B1
(45) Date of Patent: Feb. 13, 2018

(54) METHOD FOR DETERMINING WHETHER AN INDIVIDUAL ENTERS A PRESCRIBED VIRTUAL ZONE USING SKELETAL TRACKING AND 3D BLOB DETECTION

(71) Applicant: CERNER INNOVATION, INC., Kansas City, KS (US)

(72) Inventor: Neil Kusens, Sherman Oaks, CA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 14/727,434

(22) Filed: Jun. 1, 2015

(51) Int. Cl.
| | |
|---|---|
| *G06K 9/00* | (2006.01) |
| *G08B 21/04* | (2006.01) |
| *G06T 7/20* | (2017.01) |
| *G06K 9/32* | (2006.01) |
| *G08B 23/00* | (2006.01) |
| *A61B 5/11* | (2006.01) |

(Continued)

(52) U.S. Cl.
CPC .......... *G08B 21/043* (2013.01); *A61B 5/1117* (2013.01); *A61B 5/1128* (2013.01); *G06K 9/00771* (2013.01); *G06K 9/3241* (2013.01); *G06T 7/20* (2013.01); *G08B 23/00* (2013.01); *G08B 25/14* (2013.01); *G06K 2009/3291* (2013.01); *G06T 2207/10021* (2013.01)

(58) Field of Classification Search
CPC .................................. G06K 9/00; A61B 5/00
USPC .......... 382/103, 107, 236; 348/169–172, 352
See application file for complete search history.

(56) References Cited

U.S. PATENT DOCUMENTS

| | | |
|---|---|---|
| 4,857,716 A | 8/1989 | Gombrich et al. |
| 5,031,228 A | 7/1991 | Lu |

(Continued)

FOREIGN PATENT DOCUMENTS

DE 19844918 A1 4/2000

OTHER PUBLICATIONS

Pending U.S. Application by same inventor Neil Kusens, U.S. Appl. No. 14/084,588, filed Nov. 19, 2013, entitled "Method for Determining Whether an Individual Leaves a Prescribed Virtual Perimeter".

(Continued)

*Primary Examiner* — Abolfazl Tabatabai
(74) *Attorney, Agent, or Firm* — Shook, Hardy & Bacon, LLP

(57) ABSTRACT

A method and system that allows healthcare providers, hospitals, skilled nursing facilities and other persons to monitor disabled, elderly or other high-risk individuals to prevent or reduce falls and/or mitigate the impact of a fall by delivering automated notification of "at risk" behavior and falls by such an individual being monitored where assistance is required. Two systems are used to identify patients, a skeletal tracking system, which identifies patients by biometric indicators, and a virtual blob detection system. In the virtual blob system, the monitored individual is virtually represented as a blob object of at least a specific size by a computerized monitoring system and such system detects and alerts when the blob object enters or crosses into a virtually defined or designated blob detection zone and remains in the zone for at least a predetermined period of time. These systems may be used concurrently, or one system may be used primarily, with the other system acting as a failsafe.

20 Claims, 19 Drawing Sheets

(51) Int. Cl.
*G08B 25/14* (2006.01)
*H04N 5/225* (2006.01)

(56) References Cited

U.S. PATENT DOCUMENTS

| | | | |
|---|---|---|---|
| 5,448,221 A * | 9/1995 | Weller | G08B 21/22 |
| | | | 340/539.21 |
| 5,482,050 A | 1/1996 | Smokoff et al. | |
| 5,798,798 A | 8/1998 | Rector et al. | |
| 5,915,379 A | 6/1999 | Wallace et al. | |
| 5,942,986 A | 8/1999 | Shabot et al. | |
| 6,050,940 A | 4/2000 | Braun et al. | |
| 6,095,984 A | 8/2000 | Amano et al. | |
| 6,160,478 A | 12/2000 | Jacobsen et al. | |
| 6,174,283 B1 | 1/2001 | Nevo et al. | |
| 6,188,407 B1 | 2/2001 | Smith et al. | |
| 6,269,812 B1 | 8/2001 | Wallace et al. | |
| 6,287,452 B1 | 9/2001 | Allen et al. | |
| 6,322,502 B1 * | 11/2001 | Schoenberg | G06F 19/322 |
| | | | 600/300 |
| 6,369,838 B1 | 4/2002 | Wallace et al. | |
| 6,429,869 B1 | 8/2002 | Kamakura et al. | |
| 6,614,349 B1 * | 9/2003 | Proctor | G08B 13/1427 |
| | | | 340/5.92 |
| 6,727,818 B1 | 4/2004 | Wildman et al. | |
| 6,804,656 B1 | 10/2004 | Rosenfeld et al. | |
| 7,323,991 B1 | 1/2008 | Eckert et al. | |
| 7,420,472 B2 * | 9/2008 | Tran | A61B 5/103 |
| | | | 340/539.1 |
| 7,612,679 B1 | 11/2009 | Fackler et al. | |
| 7,724,147 B2 * | 5/2010 | Brown | G06F 19/3418 |
| | | | 340/286.07 |
| 7,756,723 B2 | 7/2010 | Rosow et al. | |
| 7,908,153 B2 | 3/2011 | Scherpbier et al. | |
| 7,945,457 B2 | 5/2011 | Zaleski | |
| 7,972,140 B2 | 7/2011 | Renaud | |
| 8,237,558 B2 | 8/2012 | Seyed Momen et al. | |
| 8,273,018 B1 | 9/2012 | Fackler et al. | |
| 8,432,263 B2 | 4/2013 | Kunz | |
| 8,529,448 B2 * | 9/2013 | McNair | A61B 5/00 |
| | | | 600/300 |
| 8,565,500 B2 | 10/2013 | Neff | |
| 8,620,682 B2 | 12/2013 | Bechtel et al. | |
| 8,769,153 B2 | 7/2014 | Dziubinski | |
| 8,902,068 B2 | 12/2014 | Bechtel et al. | |
| 8,917,186 B1 | 12/2014 | Grant | |
| 9,072,929 B1 | 7/2015 | Rush et al. | |
| 9,129,506 B1 | 9/2015 | Kusens | |
| 9,147,334 B2 | 9/2015 | Long et al. | |
| 9,159,215 B1 | 10/2015 | Kusens | |
| 9,305,191 B2 | 4/2016 | Long et al. | |
| 9,538,158 B1 | 1/2017 | Rush et al. | |
| 9,741,227 B1 * | 8/2017 | Kusens | G08B 21/043 |
| 2002/0015034 A1 | 2/2002 | Malmborg | |
| 2002/0077863 A1 | 6/2002 | Rutledge et al. | |
| 2002/0183976 A1 | 12/2002 | Pearce | |
| 2003/0037786 A1 | 2/2003 | Biondi et al. | |
| 2003/0070177 A1 | 4/2003 | Kondo et al. | |
| 2003/0092974 A1 | 5/2003 | Santoso et al. | |
| 2003/0095147 A1 | 5/2003 | Daw | |
| 2003/0140928 A1 | 7/2003 | Bui et al. | |
| 2003/0227386 A1 | 12/2003 | Pulkkinen et al. | |
| 2004/0019900 A1 | 1/2004 | Knightbridge et al. | |
| 2004/0052418 A1 | 3/2004 | DeLean | |
| 2004/0054760 A1 | 3/2004 | Ewing et al. | |
| 2004/0097227 A1 | 5/2004 | Siegel | |
| 2004/0116804 A1 | 6/2004 | Mostafavi | |
| 2004/0193449 A1 | 9/2004 | Wildman et al. | |
| 2005/0038326 A1 | 2/2005 | Mathur | |
| 2005/0231341 A1 | 10/2005 | Shimizu | |
| 2005/0249139 A1 | 11/2005 | Nesbit | |
| 2006/0004606 A1 | 1/2006 | Wendl | |
| 2006/0089541 A1 | 4/2006 | Braun et al. | |
| 2006/0092043 A1 | 5/2006 | Lagassey | |
| 2006/0107295 A1 | 5/2006 | Margis et al. | |
| 2006/0145874 A1 | 7/2006 | Fredriksson et al. | |
| 2006/0261974 A1 | 11/2006 | Albert et al. | |
| 2007/0085690 A1 | 4/2007 | Tran | |
| 2007/0279219 A1 | 12/2007 | Warriner | |
| 2008/0002860 A1 | 1/2008 | Super et al. | |
| 2008/0004904 A1 | 1/2008 | Tran | |
| 2008/0087719 A1 | 4/2008 | Sahud | |
| 2008/0249376 A1 | 10/2008 | Zaleski | |
| 2009/0091458 A1 | 4/2009 | Deutsch | |
| 2009/0099480 A1 | 4/2009 | Salgo et al. | |
| 2009/0224924 A1 | 9/2009 | Thorp | |
| 2009/0278934 A1 | 11/2009 | Ecker et al. | |
| 2009/0322513 A1 | 12/2009 | Hwang et al. | |
| 2010/0117836 A1 | 5/2010 | Seyed Momen et al. | |
| 2010/0176952 A1 | 7/2010 | Bajcsy et al. | |
| 2010/0188228 A1 | 7/2010 | Hyland | |
| 2010/0205771 A1 | 8/2010 | Pietryga et al. | |
| 2010/0245577 A1 | 9/2010 | Yamamoto | |
| 2010/0285771 A1 | 11/2010 | Peabody | |
| 2011/0018709 A1 | 1/2011 | Kombluh | |
| 2011/0025493 A1 | 2/2011 | Papadopoulos et al. | |
| 2011/0025499 A1 | 2/2011 | Hoy et al. | |
| 2011/0087079 A1 | 4/2011 | Aarts | |
| 2011/0102133 A1 | 5/2011 | Shaffer | |
| 2011/0175809 A1 * | 7/2011 | Markovic | A63F 13/10 |
| | | | 345/158 |
| 2011/0227740 A1 | 9/2011 | Wohltjen | |
| 2012/0026308 A1 | 2/2012 | Johnson et al. | |
| 2012/0075464 A1 | 3/2012 | Derenne et al. | |
| 2012/0092162 A1 | 4/2012 | Rosenberg | |
| 2012/0098918 A1 | 4/2012 | Murphy | |
| 2012/0154582 A1 | 6/2012 | Johnson et al. | |
| 2012/0212582 A1 | 8/2012 | Deutsch | |
| 2013/0120120 A1 | 5/2013 | Long et al. | |
| 2013/0122807 A1 | 5/2013 | Tenarvitz et al. | |
| 2013/0184592 A1 | 7/2013 | Venetianer et al. | |
| 2013/0309128 A1 | 11/2013 | Voegeli et al. | |
| 2013/0332184 A1 | 12/2013 | Burnham et al. | |
| 2014/0039351 A1 | 2/2014 | Mix et al. | |
| 2014/0070950 A1 | 3/2014 | Snodgrass | |
| 2014/0085501 A1 | 3/2014 | Tran | |
| 2014/0155755 A1 | 6/2014 | Pinter et al. | |
| 2014/0191861 A1 | 7/2014 | Scherrer | |
| 2014/0267625 A1 | 9/2014 | Clark et al. | |
| 2014/0327545 A1 | 11/2014 | Bolling et al. | |
| 2014/0333744 A1 | 11/2014 | Baym et al. | |
| 2014/0354436 A1 | 12/2014 | Nix et al. | |
| 2014/0365242 A1 | 12/2014 | Neff | |
| 2015/0206415 A1 | 7/2015 | Wegelin et al. | |
| 2015/0278456 A1 | 10/2015 | Bermudez Rodriguez et al. | |
| 2016/0022218 A1 | 1/2016 | Hayes et al. | |
| 2016/0267327 A1 | 9/2016 | Franz et al. | |

OTHER PUBLICATIONS

Pending U.S. Application by same inventor Neil Kusens, U.S. Appl. No. 14/575,850, filed Dec. 18, 2014, entitled "Method and Process for Determining Whether an Individual Suffers a Fall Requiring Assistance".

Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/613,866, filed Feb. 4, 2015, entitled "Method and System for Determining Whether an Individual Takes Appropriate Measures to Prevent the Spread of Healthcare Associated Infections Along With Centralized Monitoring".

Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".

(56) References Cited

OTHER PUBLICATIONS

Pending U.S. Application by same inventor Neil Kusens, U.S. Appl. No. 13/543,816, filed Jul. 7, 2012, entitled "Method and Process for Determining Whether an Individual Suffers a Fall Requiring Assistance".
Pending U.S. Application by same inventor Neil Kusens, U.S. Appl. No. 14/724,969, filed May 29, 2015, entitled "Method and Process for Determining Whether an Individual Suffers a Fall Requiring Assistance".
Pending U.S. Application by same inventor Neil Kusens, U.S. Appl. No. 14/728,762, filed Jun. 2, 2015, entitled "Method for Determining Whether an Individual Leaves a Prescribed Virtual Perimeter".
Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".
Pending U.S. Application by same inventor Neil Kusens, U.S. Appl. No. 14/743,499, filed Jun. 18, 2015, entitled "System for Determining Whether an Individual Suffers a Fall Requiring Assistance".
Pending U.S. Application by same inventor Neil Kusens, U.S. Appl. No. 14/743,447, filed Jun. 18, 2015, entitled "System for Determining Whether an Individual Suffers a Fall Requiring Assistance".
Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Non-Final Office Action dated Dec. 30, 2013 in U.S. Appl. No. 13/543,816, 9 pages.
Final Office Action dated Jun. 17, 2014 in U.S. Appl. No. 13/543,816, 15 pages.
Non-Final Office Action dated Dec. 1, 2014 in U.S. Appl. No. 13/543,816, 18 pages.
Non-Final Office Action dated Jul. 16, 2014 in U.S. Appl. No. 14/084,588, 12 pages.
Final Office Action dated Dec. 19, 2014 in U.S. Appl. No. 14/084,588, 24 pages.
Notice of Allowance dated Jun. 5, 2015 in U.S. Appl. No. 13/543,816, 5 pages.
Non-Final Office Action dated Oct. 7, 2015 in U.S. Appl. No. 14/339,397, 16 pages.
Non-Final Office Action dated Feb. 11, 2016 in U.S. Appl. No. 14/724,969, 14 pages.
Non-Final Office Action dated Mar. 11, 2016 in U.S. Appl. No. 14/575,850, 10 pages.
Non-Final Office Action dated May 23, 2016 in U.S. Appl. No. 14/743,499, 5 pages.
Notice of Allowance dated May 31, 2016 in U.S. Appl. No. 14/743,447, 8 pages.
Notice of Allowance dated Jun. 22, 2016 in U.S. Appl. No. 14/743,447, 4 pages.
Notice of Allowance dated Jun. 27, 2016 in U.S. Appl. No. 14/728,762, 14 pages.
Notice of Allowance dated Jul. 18, 2016 in U.S. Appl. No. 14/743,264, 16 pages.
Notice of Allowance dated Aug. 26, 2016 in U.S. Appl. No. 14/743,447, 5 pages.
Notice of Allowance dated Sep. 19, 2016 in U.S. Appl. No. 14/743,499, 5 pages.
Notice of Allowance dated Oct. 14, 2016 in U.S. Appl. No. 14/743,264, 14 pages.
Notice of Allowance dated Nov. 9, 2016 in U.S. Appl. No. 14/743,264, 14 pages.
Notice of Allowance dated Nov. 14, 2016 in U.S. Appl. No. 14/743,447, 5 pages.
Non-Final Office Action dated Jan. 11, 2017 in U.S. Appl. No. 14/611,363, 19 pages.
Non-Final Office Action dated Feb. 23, 2017 in U.S. Appl. No. 14/757,877, 24 pages.
First Action Interview Preinterview Communication dated Feb. 24, 2017 in U.S. Appl. No. 15/395,716, 6 pages.
Non-Final Office Action dated Apr. 5, 2017 in U.S. Appl. No. 14/623,349, 15 pages.
Non-Final Office Action dated Apr. 11, 2017 in U.S. Appl. No. 15/285,416, 13 pages.
Notice of Allowance dated Apr. 19, 2017 in U.S. Appl. No. 15/395,716, 5 pages.
Notice of Allowance dated Apr. 21, 2017 in U.S. Appl. No. 14/724,969, 9 pages.
Final Office Action dated Apr. 28, 2017 in U.S. Appl. No. 14/757,593, 20 pages.
Final Office Action dated Jul. 28, 2016 in U.S. Appl. No. 14/723,969, 26 pages.
Non-Final Office Action dated May 31, 2017 in U.S. Appl. No. 14/599,498, 24 pages.
Non-Final Office Action dated Apr. 27, 2017 in U.S. Appl. No. 15/395,526, 16 pages.
Non-Final Office Action dated May 8, 2017 in U.S. Appl. No. 15/395,250, 19 pages.
Notice of Allowance dated Jul. 24, 2017 in U.S. Appl. No. 15/395,716, 5 pages.
Non-Final Office Action dated Aug. 16, 2017 in U.S. Appl. No. 14/757,593, 8 pages.
Final Office Action dated Aug. 23, 2017 in U.S. Appl. No. 15/285,416, 16 pages.
Notice of Allowance dated Sep. 21, 2017 in U.S. Appl. No. 15/395,526, 13 pages.
Notice of Allowance dated Sep. 26, 2017 in U.S. Appl. No. 15/395,250, 13 pages.
Final Office Action dated Sep. 29, 2017 in U.S. Appl. No. 14/757,877, 22 pages.
Final Office Action dated Oct. 4, 2017 in U.S. Appl. No. 14/623,349, 30 pages.
Final Office Action dated Oct. 12, 2017 in U.S. Appl. No. 14/599,498, 28 pages.
Notice of Allowance dated Oct. 20, 2017 in U.S. Appl. No. 15/279,054, 14 pages.
First Action Interview Pre-Interview Communication dated Nov. 22, 2017 in U.S. Appl. No. 15/134,189, 4 pages.
Virtual Patient Observation: Centralize Monitoring of High-Risk Patients with Video-Cisco Video Surveillance Manager, https://www.cisco.com/c/en/us/products/collateral/physical-security/video-surveillance-manager/white paper_C11-715263.pdf.
Notice of Allowance dated Dec. 6, 2017 in U.S. Appl. No. 15/395,716, 5 pages.
Final Office Action dated Dec. 12, 2017 in U.S. Appl. No. 14/575,850, 10 pages.

* cited by examiner

Figure 7

- Virtual Blob Detection Zone(s)
- Bed Zone
- Auto Bed Zone (Select Patient)
- Auto Bed Zone (Auto-select)
- Saved Zones
- Clear All
- Rails (Trip Wires)

METHOD FOR DETERMINING WHETHER AN INDIVIDUAL ENTERS A PRESCRIBED VIRTUAL ZONE USING SKELETAL TRACKING AND 3D BLOB DETECTION

FIELD OF THE DISCLOSURE

The present disclosure is generally directed to patient monitoring systems and particularly to a system and method for monitoring patients in a manner which prevents or reduces patient falls.

BACKGROUND

According to recent studies, falls are a leading cause of death among people over the age of 65 years and 10% of the fatal falls for patients over 65 years of age occur in a hospital setting. For the general population, studies estimate that patient falls occur in 1.9 to 3% of all acute care hospitalizations. Of these hospital-based falls, approximately 30% will result in a serious injury with the cost to care for these injuries estimated to reach $54.9 billion per year by 2020. Current technologies that exist to assist in the prevention of falls are limited in their capabilities. These include pressure pads on the bed that trigger an alert when no pressure is detected on the pad, pressure pads on the floor and light beams that create a perimeter with alarms going off upon interruption of the beam. The pressure pads are ineffective as they do not prevent the fall but rather alert after the fact when it is too late. Additionally they are prone to false positive alerts. The light beams are also prone to false alerts when the patient or visitor simply reaches through it or the caregiver breaks the beam while delivering medication, food, drink or conducting a procedure on the patient. The present disclosure is directed to addressing these above-described shortcomings with current technology.

SUMMARY OF THE DISCLOSURE

Generally disclosed is a novel method and system that allows healthcare providers, hospitals, skilled nursing facilities and other persons to monitor disabled, elderly or other high-risk individuals and utilize the described technology to prevent or reduce falls and/or mitigate the impact of a fall by delivering automated notification of "at risk" behavior and/or falls by such an individual being monitored, especially falls and/or behavior where assistance is required, using a skeletal tracking system and a virtual blob detection system.

With skeletal tracking alone, there can be factors affecting the cameras/image-video quality which affects the ability of the detection/monitoring system to detect a skeleton. Such factors, especially in a hospital, include, but are not limited to, sheets/blankets covering a patient, trays positioned over the bed hiding the patient and the patient blending into the bed and not having a skeleton recognized.

With blob detection alone, there can be an increase in false positives in detecting falls and "at risk" behavior. These false positives can occur because blob detection does not differentiate between types of 3D objects. Blankets, treys, caretakers, or other 3D objects can trigger an automated notification. Blob recognition also does not differentiate between parts of the body.

The present disclosure use of a skeletal tracking system with a virtual blob detection system addresses or at least reduces the shortcomings of both systems. Skeletal tracking can be used to reduce or eliminate false positives generated by a virtual blob detection system. Virtual blob detection relies on a 3D object detection which doesn't matter how much of the person is viewable by the camera or if other objects are blocking the view of the camera. Even in poor lighting condition both the virtual blob detection system and skeletal tracking system can still capture and/or recognize movement as the system can use an IR Depth Map to perform the blob and/or skeletal detection which doesn't rely on lighting conditions.

The present disclosure uses both a skeletal tracking system and a virtual blob detection system to track whether an individual has fallen or engaged in "at risk" behavior. When the skeletal tracking system is unable to track a skeleton, then a virtual blob detection system is used to capture and/or recognize movement. In the alternative, both a skeletal tracking and a blob detection system can monitor an individual simultaneously, and notification is delivered when either system detects a fall or "at risk" behavior.

The following non-limiting definitions are provided as aid in understanding the disclosed novel method and system:

| | |
|---|---|
| 3D Camera, Motion and Sound Sensor | All electronic device that contains one or more cameras capable of identifying individual objects, people and motion regardless of lighting conditions as well as one or more microphones to detect audio. The cameras can utilize technologies including but not limited to color RGB, CMOS sensors, infrared projectors and RF-modulated light, They may also contain microprocessors and image sensors to detect and process information both sent out and received by the various cameras. The electronic device calculates if there has been a change in location of the person or object of interest over a period of time. As a non-limiting example, an object can be at time T1 located at coordinates (x1, y1, z1) in a picture frame taken by the camera. At time T2 the object is captured by the picture frame taken by the camera at coordinates (x2, y2, z2). Based on this information, motion, speed and direction can be derived utilizing the elapsed time and comparing the two 3D coordinates over the elapsed time. As opposed to conventional motion sensors, which use captured motion to control a camera, the 3D Camera, Motion and Sound Sensor used with the method and system, uses the camera in order to compute the motion as well as the size of the object. The camera/sensors are preferably continuously on at all times during while the monitoring is occurring, regardless of whether the person or object of interest is moving or not. The object size (minimum and/or maximum) can be configured through the software within, running, operating and/or controlling the Computerized Virtual Blob Detection Monitoring System. |

| | |
|---|---|
| | The 3D Camera, Motion and Sound sensor can additionally be programmed to lock on a person and can send back to the computerized monitoring system the 3D coordinates of the joints in the person's body and a skeletal outline of the person. As a non-limiting example, a person's right arm can be at time T1 located at coordinates (x1, y1, z1) in a picture frame taken by the camera. At time T2 the right arm is captured by the picture frame taken by the camera at coordinates (x2, y2, z2). Based on this information, motion, speed and direction can be derived utilizing the elapsed time and comparing the two 3D coordinates over the elapsed time,<br>The camera preferably views the entire bed or a large portion of the bed or other area that the patient is resting at (i.e. chair, couch, etc.) simply by its placement in a manner sufficient for the monitored area to be visible to the camera. Thus, the camera does not require any triggering event to cause the camera to begin recording video and/or 3D depth data or transmitting video and/or 3D depth data to the other components of the system for analysis. As the video camera is recording or otherwise transmitting video and/or 3D depth data to the other system components at all times during monitoring, the electronic device is able to immediately track, capture andlor record the monitored individual's movements at all times within the room or monitored area and will be able to provide inkirmation as to whether and when the individual begins to move or begins to get up to move. Preferably the 3D Camera, Motion and Sound Sensor records, captures and/or streams video and/or 3D depth data. As video is technically made up of individual picture frames (i.e. 30 frames per second of video), the above reference to picture frames is referring to frames of video.<br>Whether used with skeletal tracking or the virtual blob detection, depth sensitivity comes into play with both in order to minimize false alarms, as Objects behind and in front of the patient can be effectively ignored. The preferred use of depth as a factor also differentiates the current monitoring system from motion/object detection systems that rely on 2D images,<br>The 3D Camera, Motion and Sound Sensor can be located within the room of the patient being monitored and/or potentially just outside of the patient's room. It is connected to the computerized communication and computerized monitoring systems via a data connection (TCP/IP or comparable technology). |
| Computerized Virtual Blob Detection Monitoring System | A computer system specifically designed and programmed to create virtual blob detection zones around a specific object such as, but not limited to, a hospital bed and which monitors activity based on information received from the 3D Camera, Motion and Sound sensor. The computerized monitoring system will preferably be located within the patient's room and can be connected to the centralized monitoring station at the facility but can also be located at any physical location so long as a data connection (TCP/IP or comparable technology) exists between the computerized monitoring system, the computerized communication system, centralized monitoring station and 3D Camera, Motion and Sound sensor. |
| Computerized Communication System | A computer system specifically designed and programmed to facilitate communication between the monitored patient and computerized monitoring system in the event either an object, meeting the preprogrammed or preconfigured size for a triggering object, enters the virtual blob detection zone or the computerized skeletal tracking system determines the patient has fallen or performed an "at risk" behavior. This system may include but is no limited to amplified speakers, microphones, lights, monitors, computer terminals, mobile phones and/or other technologies to allow for the electronic communication to take place. The computerized communication system will preferably be located within the patients room being monitored but certain components of the system are mobile by their nature (i.e. mobile phones, pagers, computers) and can also be located at any location so long as a data connection (TCP/IP or comparable technology) exists between the computerized monitoring system, the computerized communication system, centralized monitoring station and 3D Camera, Motion and Sound sensor. |
| Computerized Skeletal Tracking System | A computer system specifically designed and programmed to lock onto an individual and send back to the computerized monitoring system the 3D coordinates of the joints in an individual's body and a skeletal outline of the individual based on information received from the 3D Camera, Motion and Sound sensor. The computerized skeletal tracking system will preferably be located within the patient's room and can be connected to the centralized monitoring station at the facility but can also be located at any physical location so long as a data connection (TCP/IP or comparable technology) exists between the computerized skeletal tracking system, the computerized communication system, centralized monitoring station and 3D Camera, Motion and Sound sensor. |

| | |
|---|---|
| System Database | A computer database that stores records, documents or other files of all alerts generated, notifications, confirmation requests, responses, and reconfirmation requests and any other desired information concerning a triggering event or lack of triggering events. |
| Centralized Monitoring Primary Display | A computer display connected to the centralized monitoring station, showing video and audio of all patient rooms connected to the centralized monitoring station. |
| Centralized Monitoring Alert Display | A computer display connected to the centralized monitoring station, showing video and audio of any patient room where an object is deemed to have entered a virtual blob detection zone, fallen, or performed an "at risk" behavior, preferably at the moment such determination is made. |
| Caregiver | A relative, friend, individual, company or facility whose purpose is to provide assistance in daily living activities for individuals who are disabled, elderly or otherwise in needs of assistance. |

BRIEF DESCRIPTION OF THE DRAWINGS

FIGS. 5 through 17 illustrate various screen shots for configuring the system for operation including defining bed zone, virtual blob detection zone(s) and alert types;

DETAILED DESCRIPTION

Figure 1:
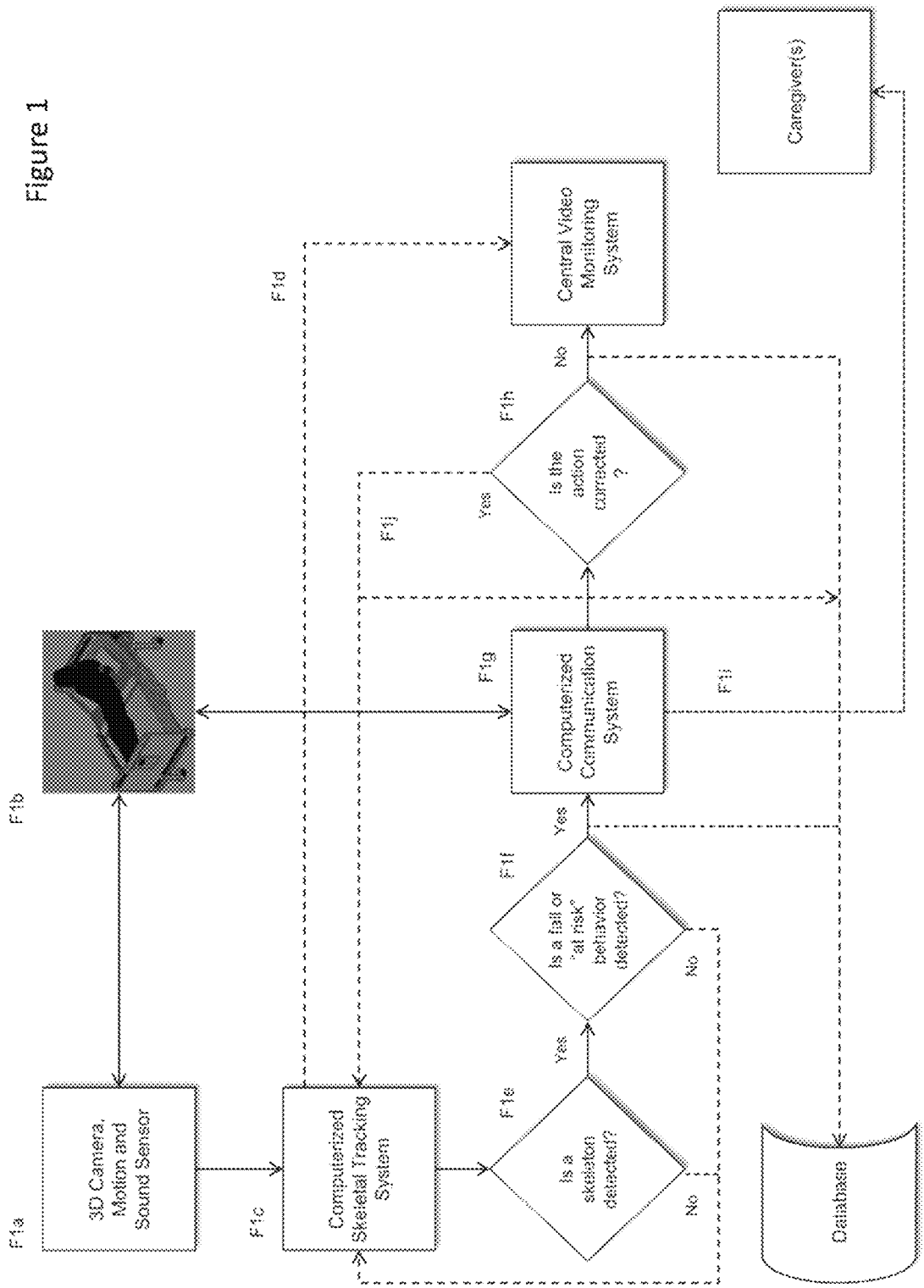
FIG. 1 is a block diagram of a computerized skeletal tracking, monitoring and alerting system and method in accordance with the present invention.

FIG. 1 illustrates a block diagram for the computerized skeletal tracking configuration, monitoring and alerting system and method of the disclosed system and method. Specifically, FIG. 1 shows the workflow for monitoring an individual's status through the use of one or more 3D Camera, Motion and Sound sensors.

At step F1a, one or more 3D Camera, Motion and/or Sound sensors can be installed in the patient's or individual's room. At step F1b, the one or more 3D Motion and Sound sensors can be configured to recognize the patient or monitored individual using biometric identifiers such as facial recognition, height, distance between points on the body, etc. The patient's body can be recognized and tracked as one or more skeletal components. Alternatively the patient can be identified by means of a user creating a three-dimensional zone around the patient through a software application stored on the Computerized Skeletal Tracking System or through the use of an electronic transmitter on the patient's or other individual's person. Once a patient is identified, the software can automatically generate or allow the user to generate a configurable three-dimensional zone or perimeter around the patient and/or the patient's bed that acts as a virtual barrier. At step F1c, data from the 3D Camera, Motion and Sound sensors can be continuously sent to a Computerized Skeletal Tracking System preferably at all times while the system is being used for monitoring. At step F1d, a continuous video feed can be sent to the Central Monitoring Primary Display preferably at all times while the system is being used for monitoring.

Figure 2:
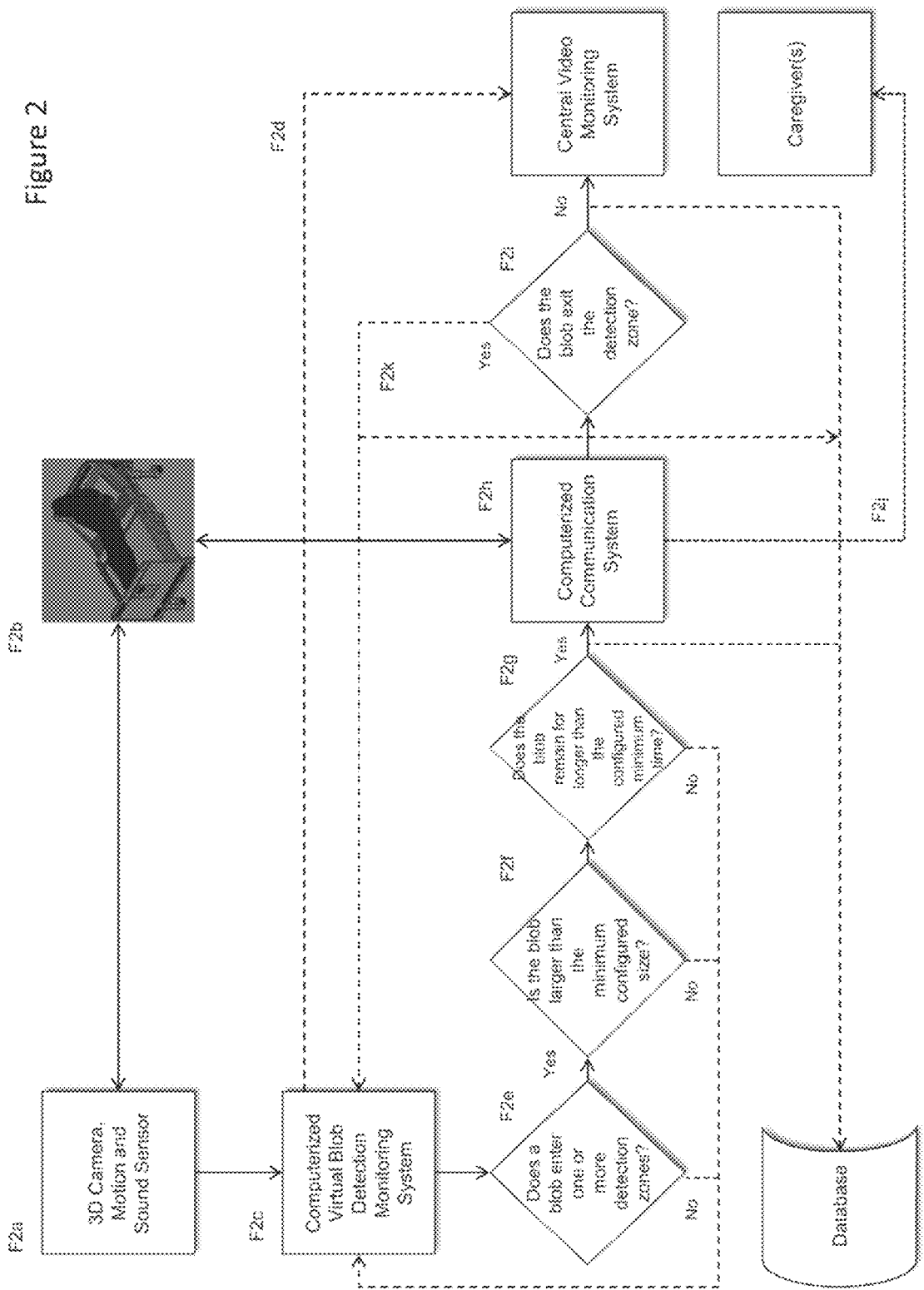
FIG. 2 is a block diagram of a virtual blob detection zone configuration, monitoring and alerting system and method in accordance with the present invention.
Figure 4:
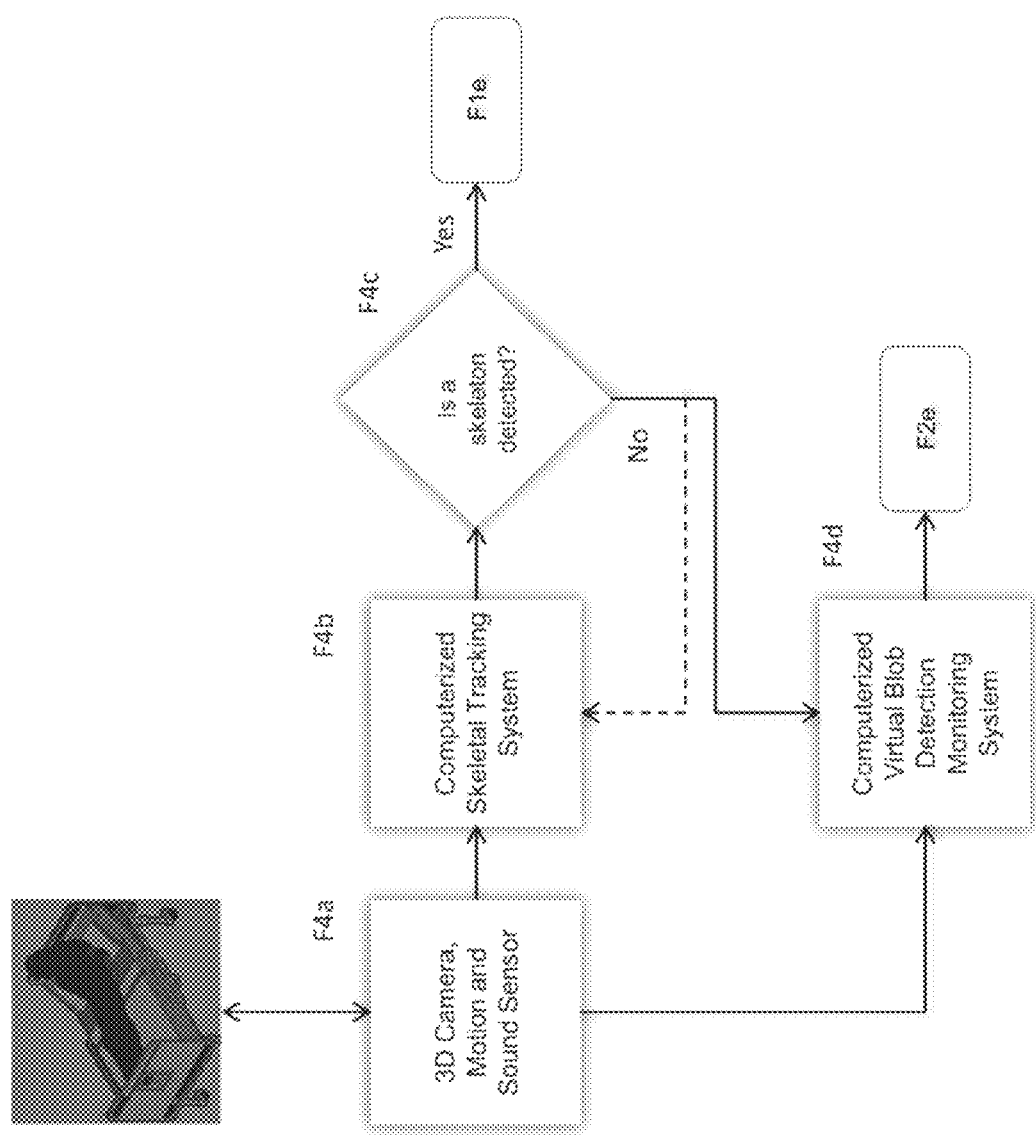
FIG. 4 is a block diagram of one embodiment of how the computerized skeletal tracking system and virtual blob detection systems can be used separately and/or concurrently in accordance with the present invention.

At step F1e, if the computerized skeletal tracking system does not detect a patient's skeleton because, for non-limiting example, the patient is covered with a sheet, blanket, tray, obscured by a caretaker or other individual, or other reason, then the computerized skeletal tracking system continues to try to identify the patient until the obstruction is removed. In some embodiments, if the computerized skeletal tracking system does not detect a patient's skeleton within a preprogrammed, configurable length of time, then the Computerized Virtual Blob Detection Monitoring System is activated and begins to monitor the patient (FIGS. 2 and 4). In some embodiments, the Computerized Virtual Blob Detection Monitoring System runs concurrently with the Computerized Skeletal Tracking System. This preprogrammed, configurable length of time can be created or selected by the user be and programmed through a software application stored on the Computerized Skeletal Tracking System.

At step F1f, if the computerized skeletal tracking system detects that the patient or any part of the patient entered the virtual barrier around the patient and/or the patient's bed, the skeletal monitoring system will alert the computerized communication system. A record can also be entered in a database to record the incident. If other individuals such as a caregiver are also detected within the patient's/monitored room at the time virtual threshold is crossed, the system can be designed or programmed such that no alert is generated and it will continue to monitor the data being sent from the 3D camera, motion and sound sensor. In this situation, generating an alarm/alert could result in a false alarm, given that there are other individual(s) with the patient, and such person(s) may be responsible for monitoring the patient and/or (even if not responsible) can assist the patient who is falling. Additionally, the person in the room should be in a better position to assist the patient as compared to the individual located at the central monitoring station. It is also within the scope of the disclosure to send alarm/alerts even if other individual(s) are in the room with the patient, as those individuals may not be the person responsible, may be elderly, may have a physical handicap preventing them from stopping a patient from falling, etc.

At step F1g the computerized communication system preferably can first issue a verbal warning to the patient that they have crossed the virtual barrier. This verbal warning can be a pre-recorded message, including, but not limited to, a pre-recorded message from any caregiver, and will advise the patient to exit the virtual barrier and return to their previous position. At step F1h, should the patient fail to exit the virtual barrier and return to their previous position in a timely manner, an alert can be generated on the Central Monitoring Alert Display System (see FIG. 3). The system database can also be updated to reflect actions taken. The system can be designed to provide visual and/or audio alerts.

At step F1i, the computerized communication system can notify caregivers or other designated persons that the individual requires assistance. Notification of caregivers can be made through phone call, text messaging, speakerphone systems, pagers, email, or other electronic means of communication if so desired and configured. At step F1j, if the patient exits the virtual barrier, the system database can be updated to reflect such. Additionally, the system will continue to monitor the patient and store all data in the system database.

FIG. 2 illustrates a block diagram for the virtual blob detection zone configuration, monitoring and alerting system and method of the disclosed system and method. Specifically, FIG. 2 shows the workflow for monitoring an individual's status through the use of one or more 3D Camera, Motion and Sound sensors.

At step F2a, one or more 3D Camera, Motion and/or Sound sensors can be installed in the patient's or individual's room. At step F2b, the one or more 3D Camera, Motion and Sound sensors can be configured to recognize the area being monitored using 3-Dimensional areas as defined by x, y, and z coordinates in relation to the 3D Camera, Motion and/or Sound Sensor. Based on the data sent/captured by the 3D Camera, Motion and/or Sound Sensor(s), the computerized virtual blob detection monitoring system is programmed to recognize any 3D object within the configured area. The patient's body is recognized and tracked as one or more blobs. Virtual blob detection zones can also be calibrated at this time. At step F1c, data from the 3D Camera, Motion and Sound sensors can be continuously sent to a Computerized Virtual Blob Detection Monitoring System preferably at all times while the system is being used for monitoring. At step F1d, a continuous video feed can be sent to the Central Monitoring Primary Display preferably at all times while the system is being used for monitoring.

At step F2e, if the computerized virtual blob detection monitoring system does not detect that the patient or any part of the patient (i.e. presented as a blob object(s)) has crossed into the designated virtual blob detection zone, it will continue monitoring. As a non-limiting example, if both hands of the patient enter the blob detection zone, the system may display and/or track as two different blobs or possibly as a single blob depending on how close the hands are to each other. If the computerized virtual blob detection monitoring system detects that the patient or any part of the patient has crossed into the designated virtual blob detection zone, it will then proceed to step F2f to determine how large the portion of the patient's body that entered the blob detection zone is. If the size of the patient's body that entered the blob detection zone is less than the configured minimum size, it will continue to monitor. Configuration is preferably through the detection system's programmed software and similar to how the zones, trip wires, etc. are configured. However, if the size of the patient's body that is within the blob detection zone is above the minimum predetermined or preprogrammed threshold for the object size, it can then proceed to step F2g. At step F2g, the system determines how long the patient's body has remained within the blob detection zone. If the patient's body has not remained in the detection zone for greater then a configured amount of time, preferably no alert is generated and the system continues to monitor (though the system can also be programmed to issue/generate an alert based solely on the system detecting a large enough blob within the detection zone for any period of time and such is also considered within the scope of the disclosure). However, if at step F2g, the patient's body has remained within the blob detection zone for greater than the minimum configured time period, the monitoring system will alert the computerized communication system. A record can also be entered in a database to record the incident. If other individuals such as a caregiver are also detected within the patient's/monitored room at the time the virtual blob detection zone threshold is crossed, the system can be designed or programmed such that no alert is generated and it will continue to monitor the data being sent from the 3D camera, motion and sound sensor. In this situation, generating an alarm/alert could result in a false alarm, given that there are other individual(s) with the patient, and such person(s) may be responsible for monitoring the patient and/or (even if not responsible) can assist the patient who is falling. The person in the room will be in a better position to assist the patient as compared to the individual located at the central monitoring station. It is also within the scope of the disclosure to send alarm/alerts even if other individual(s) are in the room with the patient, as those individuals may not be the person responsible, may be elderly, may have a physical handicap preventing them from stopping a patient from falling, etc.

At step F2h the computerized communication system preferably can first issue a verbal warning to the patient that they have entered the virtual blob detection zone. This verbal warning can be a pre-recorded message, including, but not limited to, a pre-recorded message from any caregiver, and will advise the patient to exit the virtual blob detection zone and return to their previous position. At step F2i, should the patient fail to exit the virtual blob detection zone and return to their previous position in a timely manner, an alert can be generated on the Central Monitoring Alert Display System (see FIG. 3). The system database can also be updated to reflect actions taken. The system can be designed to provide visual and/or audio alerts.

At step F2j, the computerized communication system can notify caregivers or other designated persons that the individual requires assistance. Notification of caregivers can be made through phone call, text messaging, speakerphone systems, pagers, email, or other electronic means of communication if so desired and configured. At step F2k, if the patient exits the virtual blob detection zone, the system database can be updated to reflect such. Additionally, the system will continue to monitor the patient and store all data in the system database.

Figure 3:
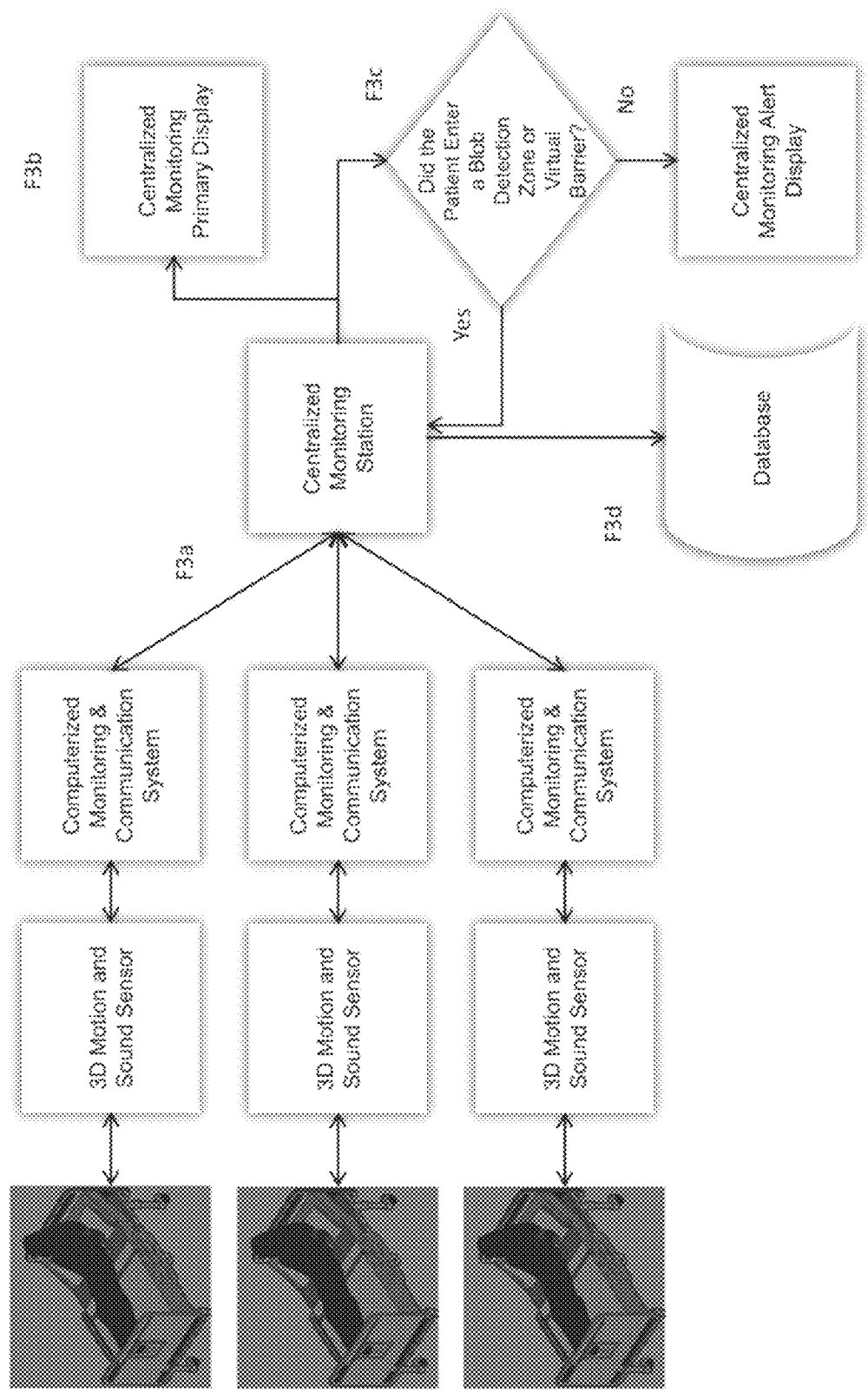
FIG. 3 is a block diagram of the centralizing monitoring and alerting system in accordance with the disclosure.

FIG. 3 illustrates a block diagram for centralized monitoring and alerting and shows the workflow for centralized monitoring and alerting of the central monitoring regarding whether an individual has entered a virtual blob detection zone through the use of 3D Camera, Motion and Sound sensors. At step F3a, one or more 3D Camera, Motion and Sound sensors are installed in and/or just outside an individual's room, home, hospital room, or other place of temporary or permanent residence and connected to the computerized monitoring and communication systems as described in FIGS. 1 and 2. The video, audio and alert data can be sent to a centralized monitoring station where the data is aggregated. Preferably, the centralized monitoring station receives data at all times from the sensors to allow the various individuals to be constantly monitored at the centralized station regardless of whether or not an individual has entered a virtual blob detection zone.

At step F3b, all video, audio and alert feeds received by the centralized monitoring station can be displayed on the centralized monitoring primary display. Alternatively, multiple centralized monitoring primary displays can be utilized based on the quantity of rooms to be monitored at a given time. At step F3c, when the centralized monitoring system receives an alert from any of the computerized monitoring and communication systems indicating that an individual in any of the monitored rooms or other locations has fallen or otherwise entered into a detection zone, the video, audio and alert information for the specific room/individual is displayed on the Centralized Monitoring Alert Display. Should the centralized monitoring station receive alerts from more than one of the computerized monitoring and communication systems indicating that an individual in a monitored room or location has entered a virtual barrier or virtual blob detection zone; the centralized monitoring alert display will display the video, audio and alerting information from all such instances preferably at the same time. If no alert is received by the centralized monitoring station, preferably nothing is displayed on the Centralized Monitoring Alert Display. At step F3d, an electronic record of any alerts received by the Centralized Monitoring Station can be stored in an electronic database, which is in communication with the Centralized Monitoring Station.

FIG. 4 illustrates a block diagram for how a computerized skeletal tracking system and a virtual blob detection monitoring system can be used concurrently or independently in the disclosed system and method. At step F4a, one or more 3D Camera, Motion and Sound sensors are installed in and/or just outside an individual's room, home, hospital room, or other place of temporary or permanent residence and connected to the computerized monitoring and communication systems as described in FIGS. 1, 2 and 3. The video, audio and/or alert data can be sent to a centralized monitoring station where the data is aggregated. Preferably, the centralized monitoring station receives data at all times from the sensors to allow the various individuals to be constantly monitored at the centralized station regardless of whether or not an individual has entered a virtual barrier or virtual blob detection zone. At step F4b, in some embodiments, both the computerized skeletal tracking system and the computerized virtual blob detection systems operate independently. In these embodiments, the skeletal tracking system performs as described in FIG. 1, and the computerized virtual blob detection monitoring system performs concurrently as described in FIG. 2. In these embodiments, it is possible that information between the two systems may conflict. As a non-limiting example, if a hospital food tray is passed to a patient, and remains within the blob detection zone for longer than the configured minimum time, the Computerized Virtual Blob Detection System may register an alert, while the Computerized Skeletal Tracking System may not. The user can select which system (if any) would take priority through a software application stored on the Computerized Skeletal Tracking System and/or the Computerized Virtual Blob Detection Monitoring System. Also, an alert can be generated only when both systems independently generate an alert, or in the alternative, an alert may be generated in the event either system generates an alert. In other embodiments, the computerized virtual blob detection monitoring system is only used when the computerized skeletal tracking system fails to identify a patient or skeleton.

Additionally, the functions of the computerized virtual blob detection monitoring system and the computerized skeletal tracking system can be performed in practice by a single system. In these embodiments, the disclosure performs the same processes described in FIGS. 1-4, but a single combined system replaces the computerized skeletal tracking system and computerized virtual blob detection monitoring system.

At step F4c, in some embodiments, if the computerized skeletal tracking system detects a skeleton, then the method proceeds to step F1e of FIG. 1. If the computerized skeletal tracking system does not detect a skeleton, within a preprogrammed, configurable length of time, then the computerized virtual blob detection monitoring system can be activated. This preprogrammed, configurable length of time can be created by the user through a software application stored on the Computerized Skeletal Tracking System. In some embodiments, while the computerized virtual blob detection monitoring system is in use, the skeletal tracking system may continue to try to detect a patient. If a patient is detected, the process proceeds to F1e of FIG. 1. At step F4d, the process then proceeds to step F2e of FIG. 2.

Figure 5:
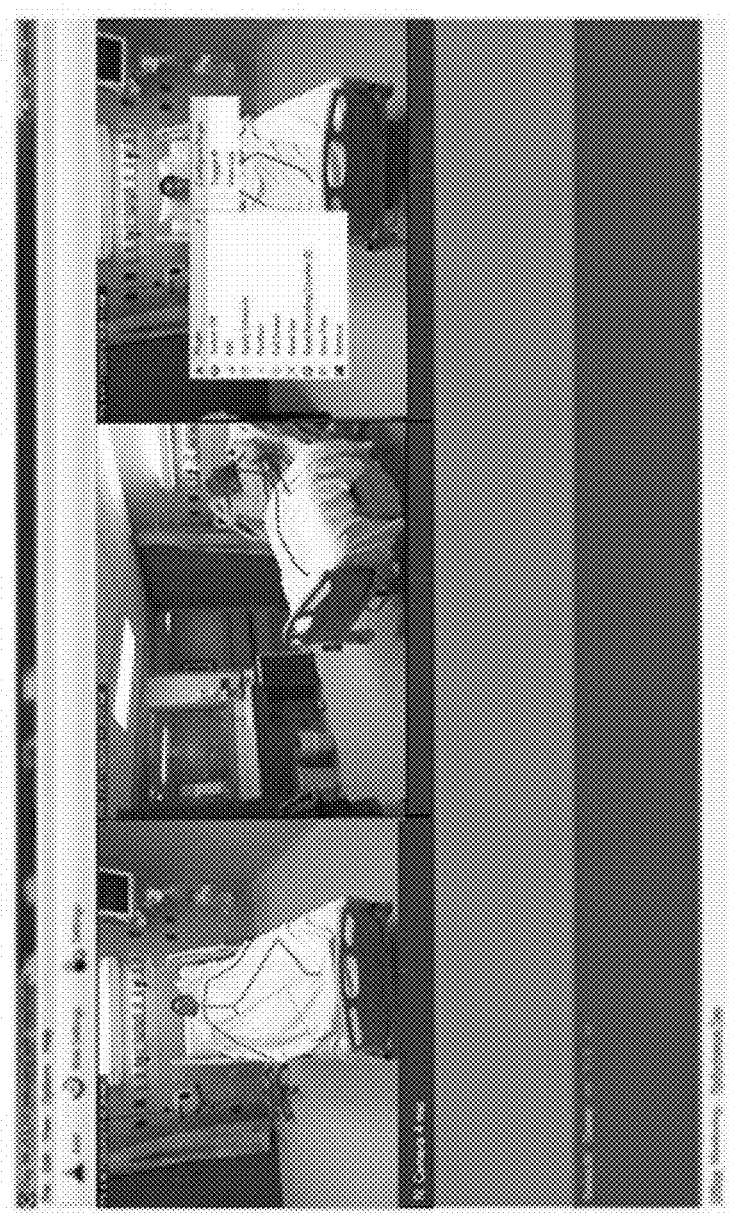

FIGS. 5 through 17 illustrate several set up screen shots for configuring the bed zone, virtual rails (trip wires), virtual blob detection zones and alert types. In FIG. 5, the bed zone, virtual trip wires and virtual blob detection zones can be configured for a given or specific 3D Camera, Motion and Sound Sensor. To begin configuration, the user can hover over the 3D Camera, Motion and Sound Sensor video window with the cursor, right-click, select plugin and then select configure plug-in. A window will popup showing the 3D Camera, Motion and Sound Sensors' feed (See FIG. 6). The user selects the icon for the type of zone or rail they wish to draw, which as a non-limiting example and illustrative purposes, can be a bed zone, virtual rail (trip wires) and virtual blob detection zone(s) (See FIG. 7).

As non-limiting examples, the icons that appear on the screen for selection can include the following symbols shown in FIG. 7. In this non-limiting example, in no particular order, some of the icons include, Bed Zone. Auto Bed Zone (Select Patient), Auto Bed Zone (Auto-select), Saved Zones, Virtual Rail (Trip Wires), Virtual Blob Detection Zone and Clear All.

Figure 6:
Figure 8:
Figure 10:

As seen in FIG. 6, to place a zone, the user clicks on the screen where he or she would like to start the zone. Then, the cursor is moved to the corner point for zone and clicked again. The user continues to select additional points until the zone is drawn to the user's satisfaction. Preferably, the user clicks on the round end point of the beginning of the zone to complete the zone (See FIG. 6). When the zone has been completed, the zone can appear and a depth range box (i.e. square, rectangle, etc. disposed over the patient on the screen) can be provided on the screen, such as, but not limited to, in the middle of the screen or zone (see FIG. 8), though any location on the screen is considered within the scope of the invention. Placing a virtual rail is done with a similar process wherein the user clicks on the screen where he or she would like to start the rail. Then the cursor is moved to the end point for the rail and the user clicks on the screen again to place the rail. As seen in FIG. 10, upon completion the zone and or rail(s) appear and has a depth range box preferably in the middle.

Figure 9:
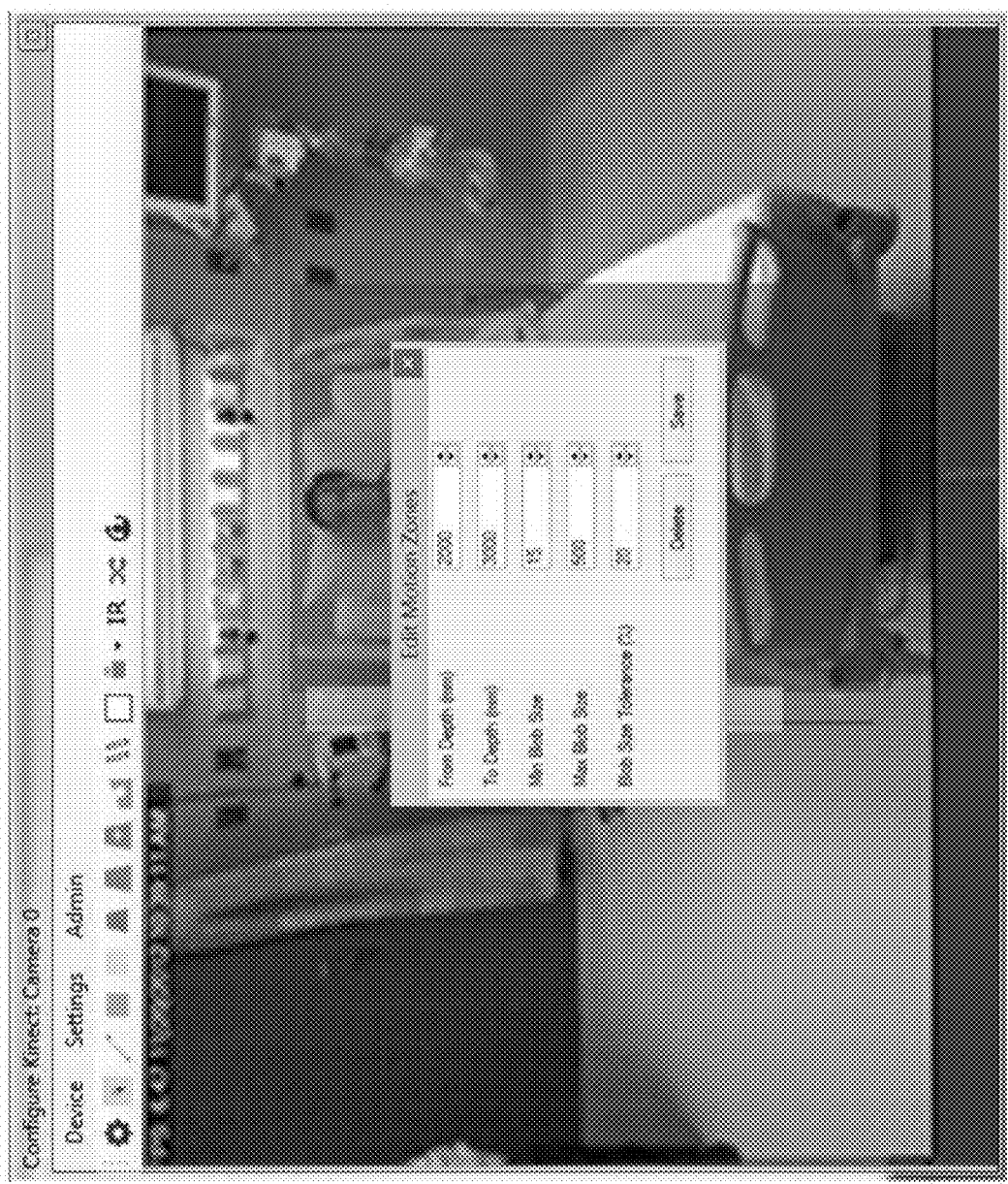

As seen in FIG. 9, the user can adjust the depth range for any given zone or rail. By preferably double clicking on the depth range box or by other conventional selection methods an Edit Depth window can appear. The user can enter in the depth ranges (preferably in millimeters (mm) though not considered limiting). Additionally, the user can enter in minimum and maximum 3D object sizes (preferably in square root pixels though not considering limiting) to detect entering the Virtual Blob Detection Zones as well as a tolerance for the size change of an object. The user can click Save button or icon when done to store the entered values.

If there are any other types of zones or rails to draw for the particular sensor, the above steps are repeated to place the next zone or rail and the depth setting can be adjusted for each if necessary. Additionally, all zones and rails can be cleared by clicking on or otherwise selecting the Clear All icon in the toolbar. Once all of the zones/rails are configured, you can close the window to finish or you have the option to save the zone/rail configuration for later use.

Figure 11:

As seen in FIG. 11, to access the main settings window, the user can click or otherwise select the Settings menu and the select Main Settings from the drop-down list. As one non-limiting alternative, the user can click on the Gear icon (✪) or other designated icon in the toolbar to access the main settings window.

Figure 12:
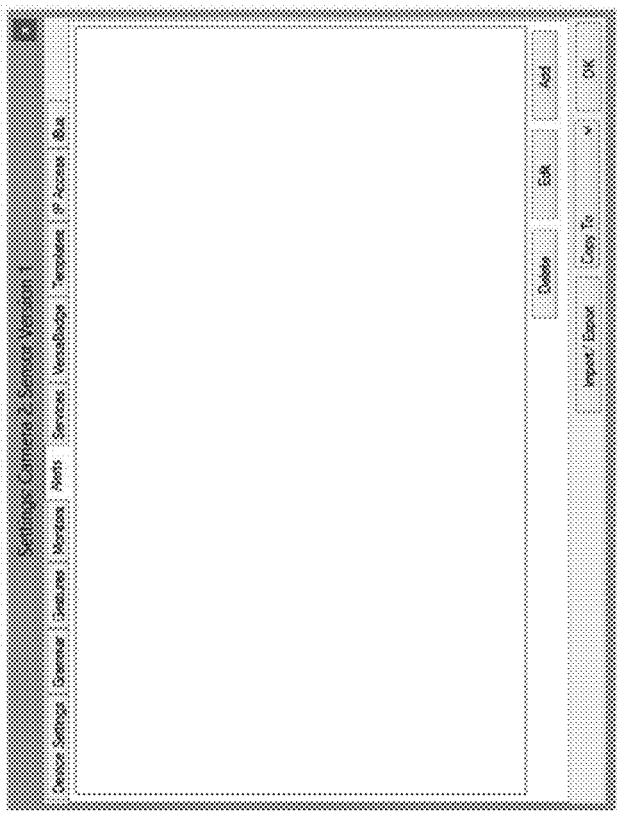
Figure 13:
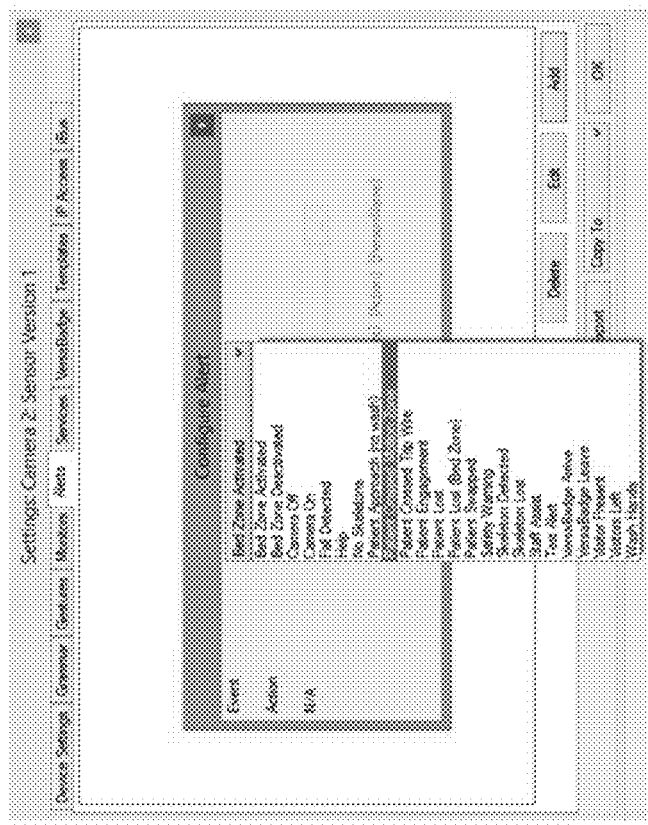
Figure 14:
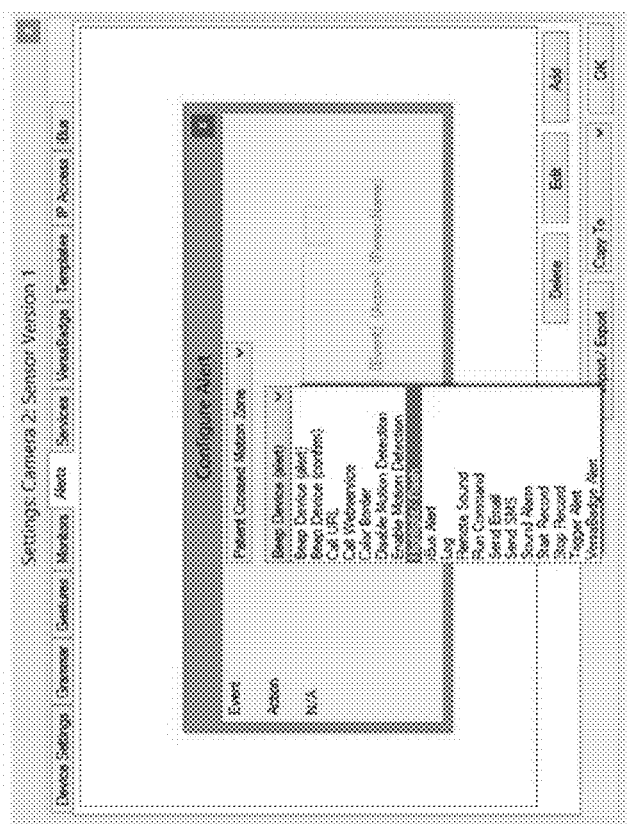
Figure 15:
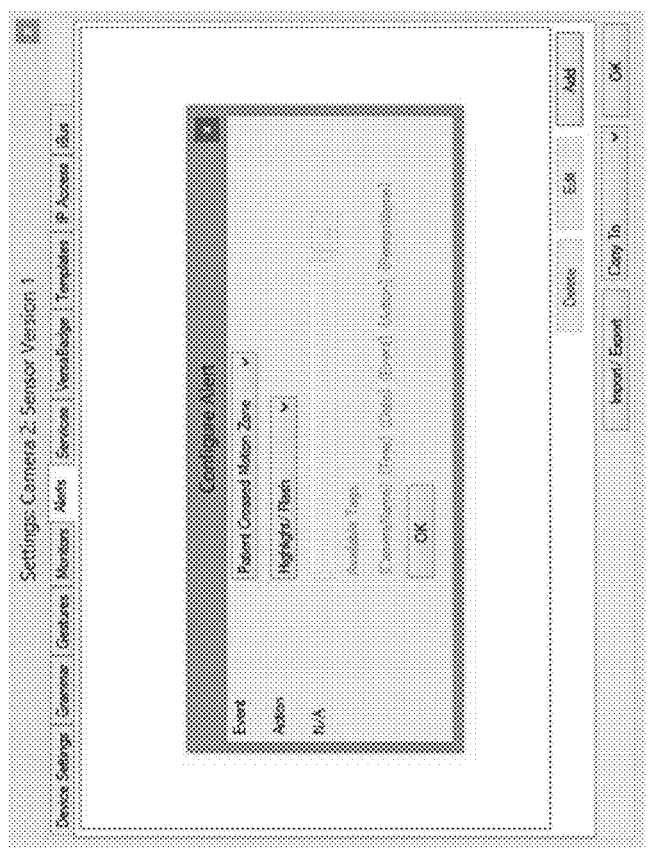
Figure 16:
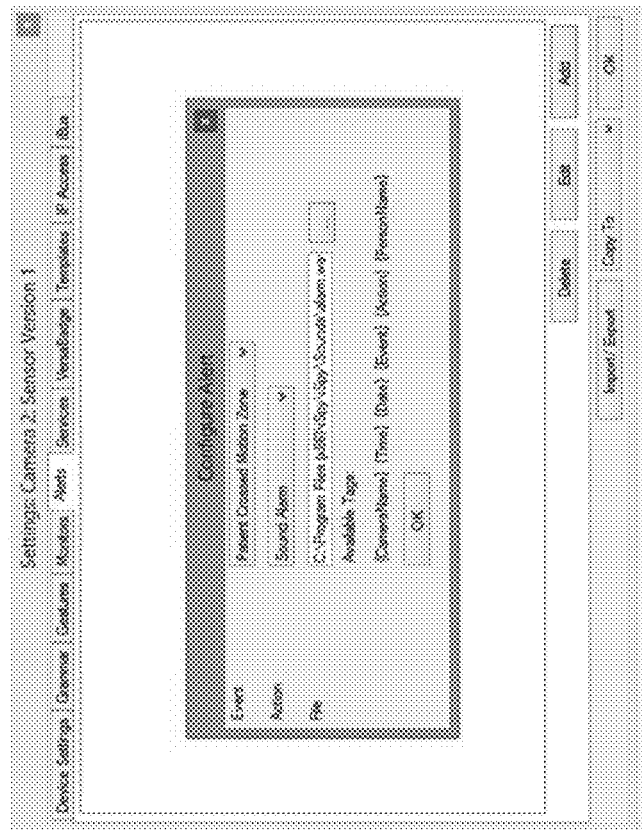
Figure 17:
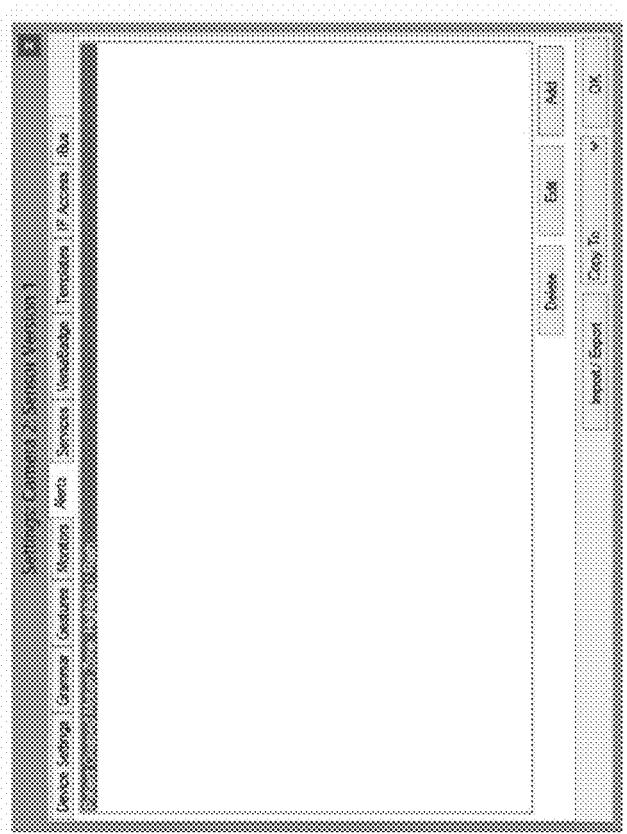

As seen in FIG. 12, for one non-limiting way to configure a new Alert, the user can select the Alerts tabs and then click on or otherwise select the Add button, which can result in the Configure Alert box appearing on the screen (See FIG. 13). As seen in FIG. 13, under the Event field, the user can then select the event from the drop down list that they wish the user wishes to send an alert on.

As seen in FIG. 13, once the Event type is selected, under the Action field, the user can select the Action he or she wishes to have the system perform when the selected Event is detected. Once the Event and Action have be selected the OK button (See FIG. 15) is can be selected to save the selected entries.

For certain Actions an additional field may need to be completed to finish the Action. If the field is required, it can appear below the Action dropdown (See FIG. 16). If no further fields are required, the Configure Alert box can display N/A (See FIG. 15) or just be blank. As mentioned above, once all settings are selected, the user clicks or otherwise selects the OK button, which causes the new Alert to be listed in the Alerts tab window. To edit an existing Alert, the user first clicks on or otherwise selects the Alert and then selects the Edit button (See FIG. 17). To delete an Alert, first highlight it can then click on the Delete button (See FIG. 17).

To add more Alerts, the user clicks or selects the Add button and repeats the above described steps. Once finished, the user clicks on or otherwise selects the bottom corner OK button to save and close the window.

Figure 18:
FIG. 18 is a non-limiting example of a centralized video monitoring system that can be used with the system and method shown in FIGS. 1 and 2.

FIG. 18 shows a non-limiting example of a centralized video monitoring system that can be used with the system and method. The window highlighted in red is a non-limiting example of an alert that can be generated when the patient fails to return to within the perimeter of the virtual safety rails.

Figure 19:
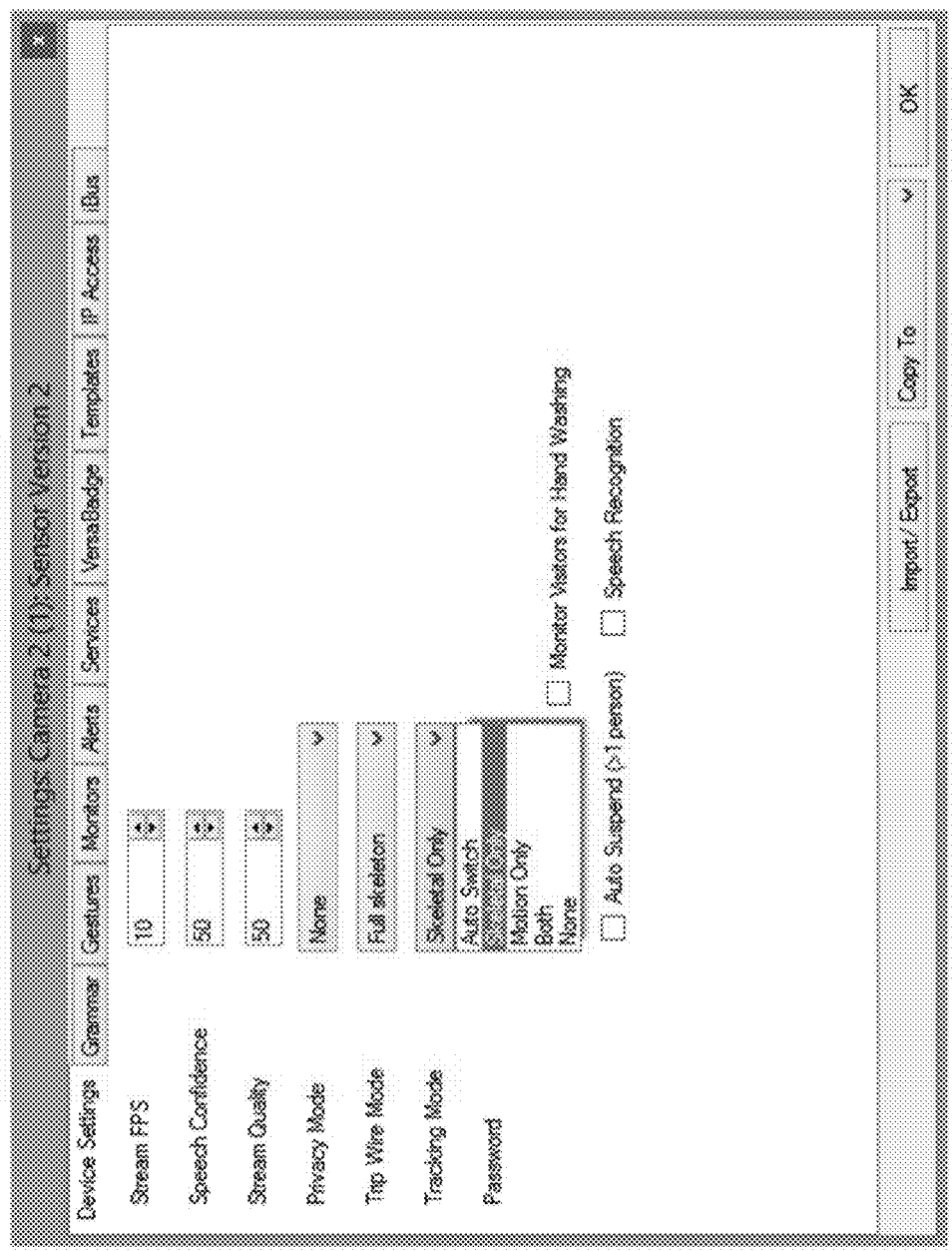
FIG. 19 is a non-limiting example of how to configure the operational mode of the system.

FIG. 19 shows a non-limiting example of how to configure the operational mode of the system. The user can select Auto-Switch in which the system will automatically switch between skeletal tracking and 3D blob detection depending on whether a skeleton is able to be tracked. Alternatively, the user may select both and cause the system to use both 3D Blob detection and skeletal tracking for alerting. Alternatively, the user can select to use either skeletal tracking or 3D blob detection solely or neither at all.

In one non-limiting embodiment, for operation the disclosed system and method can use the following components:
1. One or more 3D Camera, Motion and/or Sound Sensors
2. A Computerized Virtual Blob Detection Monitoring System
3. A Computerized Skeletal Tracking Monitoring System
4. A Computerized Communication System
5. A Centralized Monitoring Primary Display
6. A Centralized Monitoring Alert Display; and
7. Database The various components can be in electrical and/or wireless communication with each other.

Located remote is defined to mean that the centralized monitoring station, centralized monitoring primary display and/or centralized monitoring alert display is not physically located within the monitored rooms. However, the location can be on the same premises at a different location (i.e. nurse station for the premises, hospital, etc.) or a different location (i.e. monitoring station, etc.).

The automatic detection of an individual entering a prescribed virtual blob detection zone will provide significant administrative and clinical benefits to caregivers and individuals alike, including the following non-limiting public benefits:
1. Automation of determination of perimeter violation and automated notification of caregivers and/or other designated entities and/or individuals.
2. Ability to alert patients, caregivers and other individuals in time to prevent a monitored patient from getting out of bed
3. Reduction in response time for monitored individuals who have fallen and require assistance.
4. Increased survival rate for monitored individuals who have experienced a fall
5. Reduction in costs for hospitalization and medical care related to complications from a fall
6. Ability to distinguish multiple individuals and prevent false positives
7. Ability to distinguish direction of motion of prevent false positives
8. Ability to provide video feed of a monitored patient under all lighting conditions to the central video monitoring system
9. Audio and gesture based recognition to allow multiple forms of communication with patient.

Any computer/server/electronic database system (collectively "Computer System") capable of being programmed with the specific steps of the present invention can be used and is considered within the scope of the disclosure. Once specifically programmed such Computer System can preferably be considered a special purpose computer limited to the use of two or more of the above particularly described combination of steps (programmed instructions) performing two or more of the above particularly described combination of functions.

All components of the present disclosure system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. currently known and/or later developed can also be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A method for detecting when a monitored individual or any part of the monitored individual has crossed over a designated electronic perimeter, said method comprising the steps of:
   (a) electronically receiving data by a computerized monitoring system from one or more 3D Camera, Motion and Sound sensors located in the room;
   (b) tracking a monitored individual using skeletal tracking if a skeleton is detected;
   (c) tracking the monitored individual using virtual blob detection if a skeleton is not detected; and
   (d) electronically determining by the computerized monitoring system that the monitored individual has crossed a predetermined designated electronic perimeter by either electronic skeletal tracking of the monitored individual or by virtual blob detection.

2. The method for detecting of claim 1 further comprising the step of electronically alerting a computerized communication system by the computerized monitoring system when the computerized monitoring system electronically detects that the monitored individual or a part of the monitored individual has crossed over the designated electronic perimeter.

3. The method for detecting of claim 2 further comprising the step of electronically issuing an audible message to the individual by a computerized communication system to inform the individual that they have crossed over the designated electronic perimeter.

4. The method for detecting of claim 2 further comprising the step of generating an alert on a central monitoring alert display located remote from the monitored individual's room if the computerized monitoring system electronically determines that the individual crossed over the designated electronic perimeter.

5. The method for detecting of claim 2 further comprising the step of notifying a designated person associated with the individual if the computerized monitoring system electronically determines that the individual crossed over the designated electronic perimeter.

6. The method for detecting of claim 1 further comprising the step of electronically alerting a computerized communication system by the computerized monitoring system when the computerized monitoring system electronically detects that the monitored individual or a part of the monitored individual has entered or crossed into the designated electronic perimeter and remains in the designated electronic perimeter for a predetermined period of time.

7. The method for detecting of claim 6 further comprising the step of electronically issuing an audible message to the individual by a computerized communication system to inform the individual that they have entered or crossed into the designated electronic perimeter.

8. The method for detecting of claim 6 further comprising the step of generating an alert on a central monitoring alert display located remote from the monitored individual's room if the computerized monitoring system electronically determines that the individual fails to exit the designated electronic perimeter within the predetermined period of time.

9. The method for detecting of claim 6 further comprising the step of notifying a designated person associated with the individual if the computerized monitoring system electronically determines that the individual fails to exit the designated electronic perimeter within the predetermined period of time.

10. The method for detecting of claim 1 further comprising the step of electronically sending a continuous feed to remotely located centralized monitoring primary display showing the monitored area of the room by the computerized monitoring system.

11. A method for electronically monitoring for when an individual or any part of the individual crosses over a designated electronic perimeter, said method comprising the steps of:
   (a) electronically receiving data by a computerized monitoring system from one or more 3D Camera, Motion and Sound sensors located in a room;
   (b) tracking an individual using skeletal tracking if a skeleton is detected;
   (c) tracking the individual using virtual blob detection if a skeleton is not detected; and
   (d) electronically monitoring the room by the computerized monitoring system for a crossing of a designated electronic perimeter by the individual based on the data electronically received from the one or more 3D Camera, Motion and Sound sensors by either electronic skeletal tracking of the individual or by virtual blob detection.

12. The method for electronically monitoring of claim 11 wherein step (d) comprises the step of monitoring for perimeter crossings by the individual first using skeletal tracking based on skeletal points for the individual.

13. The method for electronically monitoring of claim 12 wherein if after a predetermined period of time no perimeter crossing is determined by the computerized monitoring system using skeletal tracking further comprising the step of switching to virtual blob detection monitoring for perimeter crossings by the computerized monitoring system.

14. The method for electronically monitoring of claim 11 wherein step (d) comprises the step of switching back and forth by the computerized monitoring system between skeletal tracking monitoring based on skeletal points for the individual and virtual blob detection monitoring for a perimeter crossing by the individual.

15. The method for detecting of claim 11 further comprising the step of electronically sending a continuous feed to remotely located centralized monitoring primary display showing the monitored area of the room by the computerized monitoring system.

16. The method for detecting of claim 11 further comprising the step of electronically alerting a computerized communication system by the computerized monitoring system when the computerized monitoring system electronically detects that the individual or a part of the individual has crossed over the designated electronic perimeter.

17. The method for detecting of claim 11 further comprising the step of electronically issuing an audible message to the individual by a computerized communication system to inform the individual that they have crossed over the designated electronic perimeter.

18. The method for detecting of claim 11 further comprising the step of generating an alert on a central monitoring alert display located remote from the individual's room if the computerized monitoring system electronically determines that the individual crossed over the designated electronic perimeter.

19. The method for detecting of claim 11 further comprising the step of notifying a designated person associated with the individual if the computerized monitoring system electronically determines that the individual crossed over the designated electronic perimeter.

20. A method for electronically monitoring of when an individual or any part of the individual crosses over a designated electronic perimeter, said method comprising the steps of:
- (a) electronically receiving data by a computerized monitoring system from one or more 3D Camera, Motion and Sound sensors located in a room; and
- (b) electronically monitoring the room by the computerized monitoring system for a crossing of a designated electronic perimeter by the individual based on the data electronically received from the one or more 3D Camera, Motion and Sound sensors, simultaneously using skeletal tracking monitoring based on skeletal points for the individual and virtual blob detection monitoring by the computerized monitoring system for detecting a perimeter crossing by the individual.

* * * * *